United States Patent
Bian et al.

(10) Patent No.: US 11,229,359 B2
(45) Date of Patent: Jan. 25, 2022

(54) OPHTHALMOLOGICAL DEVICE

(71) Applicant: TOMEY CORPORATION, Nagoya (JP)

(72) Inventors: Guangchun Bian, Ichinomiya (JP); Yoshito Goto, Inazawa (JP)

(73) Assignee: TOMEY CORPORATION, Nagoya (JP)

( * ) Notice: Subject to any disclaimer, the term of this patent is extended or adjusted under 35 U.S.C. 154(b) by 251 days.

(21) Appl. No.: 16/567,544

(22) Filed: Sep. 11, 2019

(65) Prior Publication Data
US 2020/0077890 A1   Mar. 12, 2020

(30) Foreign Application Priority Data
Sep. 12, 2018 (JP) .............................. JP2018-170716

(51) Int. Cl.
*A61B 3/15* (2006.01)
*A61B 3/00* (2006.01)
*A61B 3/14* (2006.01)

(52) U.S. Cl.
CPC ............ *A61B 3/152* (2013.01); *A61B 3/0008* (2013.01); *A61B 3/0083* (2013.01); *A61B 3/14* (2013.01)

(58) Field of Classification Search
CPC ......... A61B 3/152; A61B 3/0008; A61B 3/14; A61B 3/0083; A61B 3/0025; A61B 3/1005; A61B 3/165
See application file for complete search history.

(56) References Cited

U.S. PATENT DOCUMENTS

| 5,909,269 A | * | 6/1999 | Isogai | .................. A61B 3/0075 351/208 |
| 2007/0030450 A1 | * | 2/2007 | Liang | ...................... A61B 3/14 351/206 |
| 2008/0199165 A1 | * | 8/2008 | Ng | ......................... G03B 17/00 396/51 |

(Continued)

FOREIGN PATENT DOCUMENTS

| CN | 206039671 | 3/2017 |
| JP | 2000-254098 | 9/2000 |

(Continued)

OTHER PUBLICATIONS

Search Report from related EPO Appln. No. 19196554.0, dated Feb. 14, 2020.

*Primary Examiner* — Mohammed A Hasan
(74) *Attorney, Agent, or Firm* — Steven J. Grossman; Grossman, Tucker, Perreault & Pfleger PLLC

(57) ABSTRACT

An ophthalmological device according to one aspect of the present disclosure includes a support structure, an illumination light source, an observation optical system, and a controller. The support structure is configured to support a subject's face. The illumination light source is configured to illuminate a subject's eye. The observation optical system includes an imaging element configured to receive light reflecting off the subject's eye. The controller is configured to acquire, from the imaging element, a first image captured when the illumination light source is on and a second image captured when the illumination light source is off and determine whether the subject's face is placed on the support structure based on a difference between the first image and the second image.

6 Claims, 6 Drawing Sheets

(56) References Cited

U.S. PATENT DOCUMENTS

2013/0162946 A1 6/2013 Dobashi et al.
2015/0301595 A1 10/2015 Miki

FOREIGN PATENT DOCUMENTS

| JP | 5109750 | 12/2012 |
| JP | 5145555 | 2/2013 |
| JP | 2016-093253 | 5/2016 |
| JP | 6143447 | 6/2017 |
| JP | 6179320 | 8/2017 |
| WO | 2016/191827 | 12/2016 |

* cited by examiner

OPHTHALMOLOGICAL DEVICE

CROSS-REFERENCE TO RELATED APPLICATIONS

The present application claims the benefit of Japanese Patent Application No. 2018-170716 filed with the Japan Patent Office on Sep. 12, 2018, and the disclosure of which is incorporated herein by reference.

BACKGROUND

The present disclosure relates to an ophthalmological device.

As disclosed in Japanese Unexamined Patent Application Publication No. 2000-254098, ophthalmological devices configured to detect subjects have been already known. In such a known ophthalmological device, a light emitting element is turned on and off at a specific frequency so as to emit index light. A light-received signal from a light receiving element is inputted to a bypass circuit. A signal with a specific frequency is selectively extracted from the light-received signal by the bypass circuit. When a subject is present, a component of the index light reflecting off the subject is extracted. The ophthalmological device determines the presence/absence of the subject based on the extracted signal.

One type of ophthalmological devices are also known in which sensors for determining the presence/absence of subjects are provided on chin rests on which subjects' faces are to be placed.

SUMMARY

To detect subjects, the conventional devices include physical structures such as special-purpose circuits that are not directly related to ophthalmological examinations.

Accordingly, it is desirable that one aspect of the present disclosure provides an ophthalmological device that can detect a subject using a structure used for ophthalmological examinations.

The ophthalmological device according to one aspect of the present disclosure comprises a support structure, an illumination light source, an observation optical system, and a controller. The support structure is configured to support a subject's face. The illumination light source is configured to illuminate a subject's eye. The observation optical system comprises an imaging element configured to receive light reflecting off the subject's eye. The observation optical system is provided for observing the subject's eye.

The controller is configured to turn on and off the illumination light source. The controller is configured to acquire a first image from the imaging element. The first image is captured by the imaging element when the illumination light source is on. The controller is configured to acquire a second image from the imaging element. The second image is captured by the imaging element when the illumination light source is off. The controller is configured to determine whether the subject's face is placed on the support structure based on a difference between the first image and the second image.

The ophthalmological device according to one aspect of the present disclosure can determine whether the subject's face is placed on the support structure through the use of the illumination light source and the observation optical system, which are used for ophthalmological examinations.

In one aspect of the present disclosure, the controller may be configured to determine whether the subject's face is placed on the support structure based on a difference in brightness between the first image and the second image.

In one aspect of the present disclosure, the controller may be configured to determine that the subject's face is placed on the support structure when the difference in brightness between the first image and the second image is equal to or larger than a reference value, and determine that the subject's face is not placed on the support structure when the difference in brightness is smaller than the reference value.

In one aspect of the present disclosure, the ophthalmological device may further comprise a driving system configured to change a position of the observation optical system relative to the support structure. The controller may be configured to control the driving system to align the observation optical system with the subject's eye on condition that the subject's face is determined to be placed on the support structure.

In one aspect of the present disclosure, the controller may be configured to detect a position of a pupil of the subject's eye based on an image captured by the imaging element when the illumination light source is on, and control the driving system to align the observation optical system with the subject's eye based on the position of the pupil.

In one aspect of the present disclosure, the ophthalmological device may further comprise a position detection system configured to apply light to a cornea of the subject's eye and receive reflected light so as to detect a position of an apex of the cornea. The controller may be configured to perform a rough alignment processing and a fine alignment processing so as to align the observation optical system with the subject's eye in a stepwise manner.

The rough alignment processing may comprise detecting a position of a pupil of the subject's eye based on an image captured by the imaging element when the illumination light source is on, on condition that the subject's face is determined to be placed on the support structure, and controlling the driving system based on the position of the pupil detected so as to align the observation optical system with the subject's eye.

The fine alignment processing may comprise controlling the driving system based on the position of the apex of the cornea acquired from the position detection system so as to align the observation optical system with the subject's eye. The fine alignment processing may be performed after the rough alignment processing.

BRIEF DESCRIPTION OF THE DRAWINGS

An example embodiment of the present disclosure will be described hereinafter by way of example with reference to the accompanying drawings, in which.

DETAILED DESCRIPTION OF THE PREFERRED EMBODIMENTS

Figure 1:
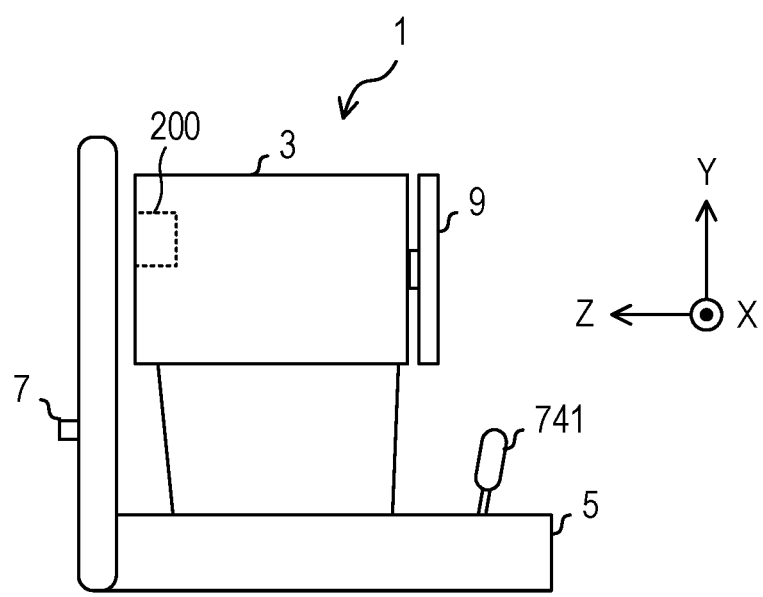
FIG. 1 is a diagram showing an external structure of an ophthalmological device.

An ophthalmological device 1, shown in FIG. 1, according to the present embodiment is configured to function as a pachymeter that measures the thickness of a cornea of an eye of a subject (subject's eye E) and as a tonometer that measures the intraocular pressure of the subject's eye E. The ophthalmological device 1 comprises a head portion 3, a main body 5, a support structure 7, and a display 9.

The head portion 3 is attached to the main body 5 in a manner movable in X (left-right), Y (up-down), and Z (front-rear) directions relative to the main body 5. The support structure 7 is configured to support the face of the subject (subject's face), specifically, the chin of the subject, and is secured to the main body 5. The display 9 is disposed in a rear portion of the head portion 3, which is on the opposite side of a front portion that faces the subject.

In an ophthalmological examination, the subject's face is placed on the support structure 7. The position of the subject's eye E is stabilized by the subject's face being supported by the support structure 7. Moreover, in the eye examination, the head portion 3 is moved in the XYZ directions relative to the main body 5 so that an optical system incorporated in the head portion 3 is aligned with the subject's eye E.

Figure 2:
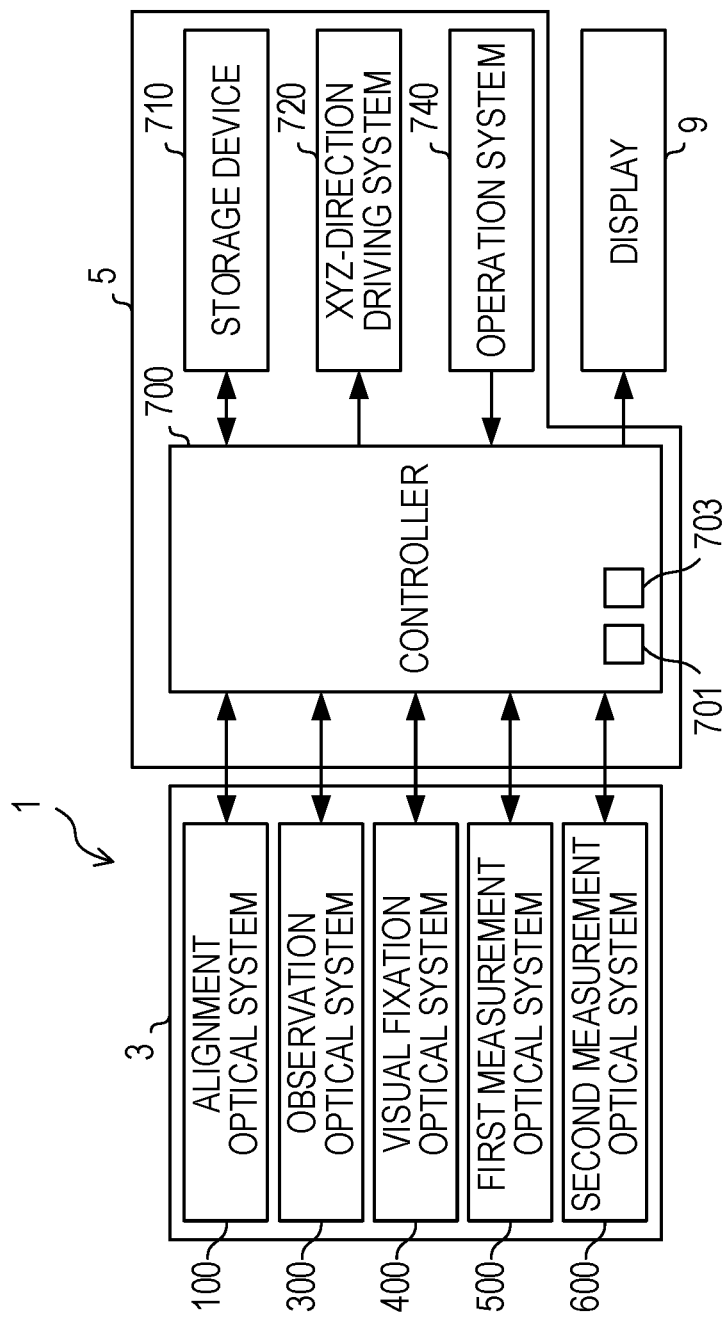
FIG. 2 is a block diagram showing an internal structure of the ophthalmological device.

As shown in FIG. 2, the head portion 3 comprises an alignment optical system 100, an observation optical system 300, a visual fixation optical system 400, a first measurement optical system 500, and a second measurement optical system 600 as the aforementioned optical system.

The main body 5 comprises a controller 700, a storage device 710, an XYZ-direction driving system 720, and an operation system 740. The controller 700 is configured to generally control the entirety of the ophthalmological device 1 and to process measurement data of the subject's eye E.

The controller 700 comprises, for example, a processor 701 and a memory 703. The processor 701 is configured to perform processes in accordance with computer programs stored in the storage device 710.

It may be understood that the processes performed by the controller 700, which will be described below, are achieved by the processor 701 performing the processes in accordance with the computer programs. The storage device 710 is composed of, for example, a nonvolatile memory such as a flash memory in which data can be electronically rewritten.

The XYZ-direction driving system 720 is configured to move the head portion 3 in the XYZ directions relative to the main body 5 based on instructions from the controller 700. The operation system 740 comprises a joystick 741 through which an examiner's operation is received.

In addition, a touchscreen (not shown) may be provided on the screen of the display 9 as part of the operation system 740. The display 9 is configured to be controlled by the controller 700 so as to show the examiner an image of the subject's eye E and various information including the intraocular pressure and the thickness of the cornea measured.

Figure 3:
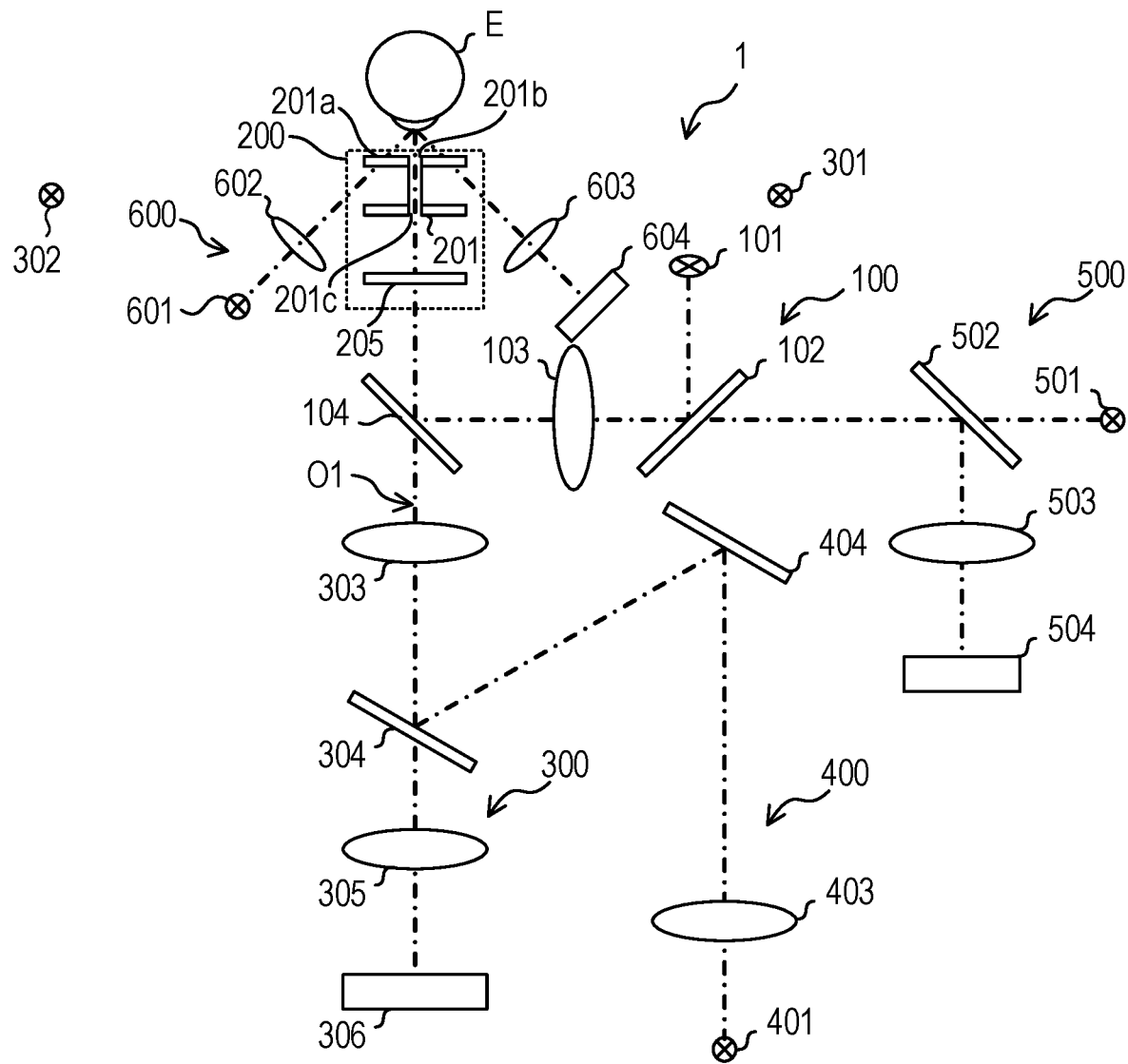
FIG. 3 is a diagram showing a structure of an optical system.

As shown in FIG. 3, the alignment optical system 100 incorporated in the head portion 3 comprises a light source 101, a hot mirror 102, an objective lens 103, and a hot mirror 104. The light source 101 is configured to output alignment light.

The alignment light from the light source 101 reflects off the hot mirror 102, passes through the objective lens 103, and reflects off the hot mirror 104. Subsequently, passing through an eyepiece 200, the alignment light is transmitted toward the cornea of the subject's eye E. The light source 101 is, for example, an LED that outputs infrared rays.

The eyepiece 200 comprises a nozzle 201 and a planar glass plate 205. The nozzle 201 comprises a transparent window member 201a, which faces the subject's eye E, and an aperture 201c. The aperture 201c is formed as an ejection path for compressed air and defines an ejection port 201b in the center of the window member 201a.

When the intraocular pressure is measured, the compressed air is ejected from the ejection port 201b through the aperture 201c toward the subject's eye E. The alignment light reflecting off the aforementioned hot mirror 104 passes through the planar glass plate 205 of the eyepiece 200 and the aperture 201c of the nozzle 201 and is applied to the subject's eye E.

The light reflects off the cornea of the subject's eye E is transmitted inside the observation optical system 300 disposed on a main optical axis O1. The observation optical system 300 comprises a two-dimensional imaging element 306. The light reflecting off the cornea of the subject's eye E is received by the two-dimensional imaging element (CCD) 306. Accordingly, the reflected light that corresponds to the alignment light is captured by the two-dimensional imaging element 306.

An image signal from the two-dimensional imaging element 306 that includes the captured image of the reflected light is processed by the controller 700. The controller 700 is configured to detect the position of the apex of the cornea of the subject's eye E in the XY directions based on the image of the reflected light included in the image signal. In this manner, the alignment optical system 100 and the observation optical system 300 function as the position detection system.

The XYZ-direction driving system 720 is configured to move the head portion 3 based on the detected position of the subject's eye E in the XY directions so as to align the head portion 3 with the subject's eye E in the XY directions.

The observation optical system 300 further comprises a light source 301, a light source 302, an objective lens 303, a Dichroic mirror 304, and an imaging lens 305. The light sources 301, 302 are disposed so as to illuminate an anterior segment area of the subject's eye E. For the light sources 301, 302, LEDs are used which output infrared rays with shorter wavelengths as compared to that of the alignment light from the light source 101. Hereinafter, the light from the light sources 301, 302 will be referred to as observation light.

The observation light from the light sources 301, 302 reflects off the subject's eye E. The reflected light penetrates the hot mirror 104, passes through the objective lens 303, the Dichroic mirror 304, and the imaging lens 305, and is received by the two-dimensional imaging element (CCD) 306. The receipt of the reflected light causes the two-dimensional imaging element 306 to capture an image of the anterior segment area of the subject's eye E. The image signal representing the captured image is outputted from the two-dimensional imaging element 306. The controller 700 controls the display 9 based on the image signal from the two-dimensional imaging element 306 to show the image of the anterior segment of the subject's eye E on the display 9.

Moreover, the visual fixation optical system 400 comprises a light source 401, a relay lens 403, and a reflective mirror 404. The light source 401 is configured to transmit light that facilitates visual fixation of the subject (hereinafter referred to as visual fixation light).

The visual fixation light passes through the relay lens 403 and reflects off the reflective mirror 404. Subsequently, the visual fixation light reflects off the Dichroic mirror 304, passes along the main optical axis O1 through the objective lens 303 and the hot mirror 104. As a result, an image is formed on the retina of the subject's eye E. Due to the visual fixation light, the subject's eye E is brought into a fixed state which enables examination of ocular characteristics, such as an intraocular pressure examination. For the light source 401, an LED is used which outputs light visible to the subject.

The first measurement optical system 500 for measuring the intraocular pressure comprises a light source 501, a semi-reflective mirror 502, a condenser lens 503, and a light receiving element 504. Light from the light source 501 (hereinafter referred to as first measurement light) penetrates the semi-reflective mirror 502, the hot mirror 102, and the objective lens 103, and reflects off the hot mirror 104. Subsequently, the first measurement light passes along the main optical axis O1 and through the planar glass plate 205 and the aperture 201c of the nozzle 201, and is applied to the cornea of the subject's eye E.

The light applied to the cornea of the subject's eye E reflects off the cornea and travels as if it goes back through the route that it has once traveled. The reflected light passes through the aperture 201c of the nozzle 201 and the planar glass plate 205 and then reflects off the hot mirror 104. The light further passes through the objective lens 103 and the hot mirror 102 and reflects off the semi-reflective mirror 502 so as to pass through the condenser lens 503 and to be received by the light receiving element 504.

In the intraocular pressure test, the compressed air is ejected from the nozzle 201 toward the cornea of the subject's eye E. In response to the ejection of the compressed air, the cornea of the subject's eye E is displaced and deformed, and thus the amount of light received by the light receiving element 504 changes. The intraocular pressure of the subject's eye E is calculated from the degree of such change in amount of the light.

For the light source 501, an LED is used which outputs infrared rays with wavelengths that are longer than that of the observation light and shorter than that of the alignment light. The wavelengths of the alignment light, the observation light, the visual fixation light, and the first measurement light are set as described above, and the reflection and/or transmission characteristics of the hot mirrors 102, 104, and the Dichroic mirror 304 are suitably set so that these four types of light are respectively transmitted along the suitable paths.

The second measurement optical system 600 for measuring the thickness of the cornea comprises a light source 601, a lens 602, a cylindrical lens 603, and a light receiving element 604. The light from the light source 601 (hereinafter referred to as second measurement light) is first collimated by the lens 602. Then, the second measurement light passes through the transparent window member 201a of the eyepiece 200 and is applied to the cornea of the subject's eye E. The second measurement light applied to the cornea reflects off the corneal endothelium and the corneal epithelium of the subject's eye E. The light reflected at these points passes through the transparent window member 201a of the eyepiece 200 and the cylindrical lens 603 so as to be received by the light receiving element 604. For the light source 601, a coherent super-luminescent diode (SLD) is used, for example. For the light source 601, not only the SLD, but also a coherent light source (diode), such as a laser diode (LD), may be alternatively used.

If a coherent light source is used as the light source 601, speckle noise may be generated and the accuracy in measuring the thickness of the cornea may be reduced. Nevertheless, it is possible to reduce the speckle noise by allowing the passage of the second measurement light that has reflected off the corneal endothelium and the corneal epithelium of the subject's eye E through the cylindrical lens 603 as described above so as to linearly shape the second measurement light.

A light-received signal transmitted from the light receiving element 604 is processed by the controller 700. The controller 700 is configured to measure the thickness of the cornea of the subject's eye E based on the difference between the positions on the light receiving surface to receive first reflected light and to receive second reflected light that are identified from the light-received signals. The first reflected light is the light reflecting off the corneal endothelium of the subject's eye E. The second reflected light is the light reflecting off the corneal epithelium.

In addition, the second measurement optical system 600 is used as a Z-direction alignment optical system prior to ophthalmological examinations. A light receiving position at which the light receiving element 604 receives the reflected light changes depending on the position of the cornea of the subject's eye E in the Z direction. The controller 700 detects the position of the cornea of the subject's eye E in the Z direction based on the light receiving position. The XYZ-direction driving system 720 adjusts the position of the head portion 3 in the Z direction relative to the subject's eye E based on the detected position.

In the ophthalmological device 1, alignment of the head portion 3 in the Z direction with the subject's eye E is automatically performed based on, for example, the image of the anterior segment of the subject's eye E shown by the image signal from the two-dimensional imaging element 306 (rough alignment), and then automatically and accurately performed based on the second measurement light (fine alignment).

As described above, alignment of the head portion 3 in the XY directions with the subject's eye E is also automatically performed in a similar manner based on the image of the anterior segment of the subject's eye E shown by the image signal from the two-dimensional imaging element 306 (rough alignment), and then is automatically and accurately performed based on the alignment light (fine alignment). If it is not possible to automatically perform the rough alignment, the rough alignment is manually performed by the examiner using the joystick 741.

Figure 4:
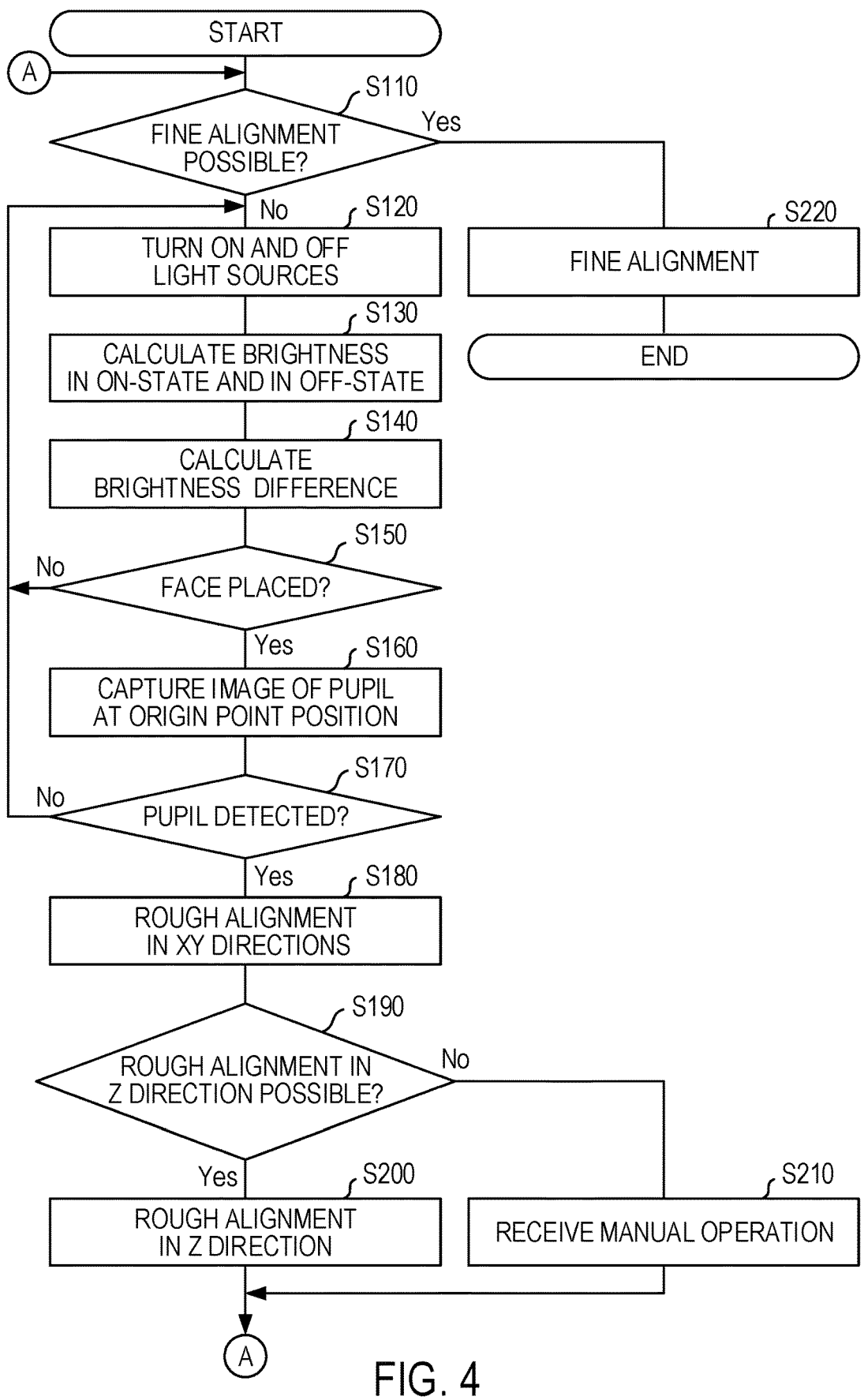
FIG. 4 is a flowchart illustrating an alignment process performed by a controller.

With reference to FIG. 4, the detail of the alignment process performed by the controller 700 will be described below. The controller 700 repeatedly performs the alignment process shown in FIG. 4 while the subject's face is placed on the support structure 7 so as to automatically align the head portion 3 with the subject's eye E.

When the alignment process is initiated, the controller 700 determines whether it is possible to perform the fine alignment processing (S110). If the position of the head portion 3 relative to the subject's eye E is within a range where the fine alignment processing can be performed, the controller 700 makes an affirmative determination in S110. If the relative position of the head portion 3 is elsewhere, the controller 700 makes a negative determination in S110.

To determine whether it is possible to perform the fine alignment processing, the controller 700 may transmit the alignment light from the light source 101 and acquire the image signal from the two-dimensional imaging element 306. If the image signal includes a component of the reflected light that correspond to that of the alignment light, and the position of the apex of the cornea is detected from the component of the reflected light, the controller 700 may determine that it is possible to perform the fine alignment processing.

Determining in S110 that it is possible to perform the fine alignment processing (S110: Yes), the controller 700 performs the fine alignment processing in S220. Then, the alignment process is completed.

Making the negative determination in S110, the controller 700 turns on and off the light sources 301, 302 (S120). The controller 700 further acquires the image signal from the two-dimensional imaging element 306 respectively when the light sources 301, 302 are on (ON-state) and when the light sources 301, 302 are off (OFF-state) (S120). The image signal acquired in the ON-state represents the image (light receiving image) captured by the two-dimensional imaging element 306 in the ON-state. The image signal in the OFF-state represents the image (light receiving image) captured by the two-dimensional imaging element 306 in the OFF-state.

Based on the acquired image signal, the controller 700 calculates a brightness B1 of the image captured in the ON-state and a brightness B2 of the image captured in the OFF-state (S130). The controller 700 further calculates the difference in brightness BD=B1–B2 between the brightness B1 in the ON-state and the brightness B2 in the OFF-state (S140).

The brightness B1 and the brightness B2 may be the sum or the average of the brightness of the pixels in the entire captured image, or may alternatively be the sum or the average of the brightness of the pixels located in a pre-defined central portion of the captured image.

Figure 5:
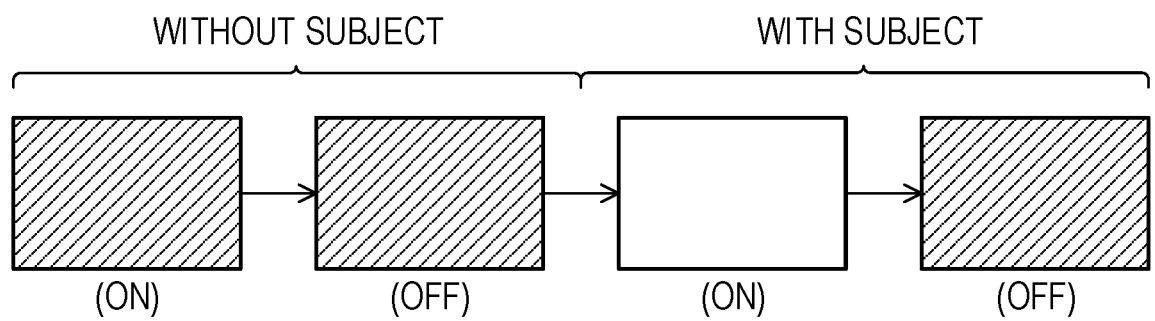
FIG. 5 is an explanatory diagram in relation to brightness.

Based on the brightness difference BD calculated as described above, the controller 700 determines whether the subject's face is placed on the support structure 7 (S150). As shown in FIG. 5, if the subject's face is not placed on the support structure 7, the light that reaches the two-dimensional imaging element 306 is mostly background light transmitted from outside of the ophthalmological device 1 through the eyepiece 200, and thus the brightness of the image captured by the two-dimensional imaging element 306 is low irrespective of whether the light sources 301, 302 are on. In FIG. 5, the low brightness state is represented by hatching.

On the other hand, if the subject's face is placed on the support structure 7, the light from the light source 301 and the light from the light source 302 reflect off the subject's face, particularly the subject's eye E, and each of the reflected light is received by the two-dimensional imaging element 306. Accordingly, the brightness of the captured image is low during the OFF-state, whereas the brightness is high during the ON-state. Utilizing such a phenomenon, the controller 700 determines, in S150, whether the subject's face is placed on the support structure 7 based on the brightness difference BD.

Specifically, the controller 700 determines that the subject's face is placed on the support structure 7 (S150: Yes) if the brightness difference BD is equal to or larger than a predetermined threshold, and determines that the subject's face is not placed on the support structure 7 (S150: No) if the brightness difference BD is not equal to or larger than the threshold.

Determining that the subject's face is not placed on the support structure 7 (S150: No), the controller 700 again turns on and off the light sources 301, 302 (S120) and then performs the processing of S130 to S150 again. When the light sources 301, 302 are turned on and off again, the turn-on and turn-off may be performed at a specified interval from the previous turn-on and turn-off.

Determining that the subject's face is placed on the support structure 7 (S150: Yes), the controller 700 places the head portion 3 in a position where the point of origin in the Z direction is located (to be referred to as origin point position) and captures an image of the subject's eye E so as to detect the pupil (S160).

Specifically, the controller 700 first causes the XYZ-direction driving system 720 to move the head portion 3 to the origin point position in the Z direction. The origin point position corresponds to a position which is within a range where the image of the pupil of the subject's eye E can be captured and where the head portion 3 is positioned the farthest from the subject's eye E in the Z direction. The head portion 3 is placed in the origin point position at this stage so as to inhibit the head portion 3 from contacting the subject (particularly, the subject's eye E) in a later stage when the head portion 3 is moved.

Subsequently, while the head portion 3 being placed in the origin point position, the controller 700 turns on the light sources 301, 302 so as to capture the image of the subject's eye E, and acquires the image signal in the ON-state from the two-dimensional imaging element 306. The image signal basically represents the captured image of the anterior segment area of the subject's eye E. The controller 700 analyzes the acquired image signal and detects a black circular area in the captured image of the anterior segment area shown by the image signal so as to detect the pupil of the subject's eye E and the position of the pupil in the XY directions.

If the pupil is detected, the controller 700 makes an affirmative determination in S170 and performs the processing of S180. On the other hand, if the pupil is not detected, the controller 700 makes a negative determination in S170 and performs the processing of S120 again.

In S180, the controller 700 performs the rough alignment processing in the XY directions based on the position of the detected pupil. Specifically, the controller 700 causes the XYZ-direction driving system 720 to move the head portion 3 in the XY directions such that the head portion 3 is aligned with the center of the detected pupil.

Subsequently, the controller 700 determines whether it is possible to perform the rough alignment processing in the Z direction (S190). Specifically, the controller 700 analyzes the image signal from the two-dimensional imaging element 306 and determines whether it is possible to calculate a distance D between the position of the reflected light of the light source 301 reflected in the pupil and the position of the reflected light of the light source 302 reflected in the pupil.

The image signal to be analyzed may be the image signal acquired through the capturing after the rough alignment processing in the XY directions (S180) is performed. More specifically, in order to make the aforementioned determination, the controller 700 may newly acquire, while the light sources 301, 302 are on, the image signal in the ON-state from the two-dimensional imaging element 306 in S190 and may analyze the newly acquired image signal. In an alternative example, the determination in S190 may be made based on the image signal acquired through the processing in S160 that is performed prior to the rough alignment processing in the XY directions.

In the present embodiment, the light sources 301, 302 are disposed on the left side and the right side of the subject's eye E. Thus, when it is possible to calculate the distance D, the position of the subject's eye E in the Z direction can be approximately located from the distance D although the calculated distance D includes an error caused by the difference in curvature of eyes of individual subjects.

Figure 6A:
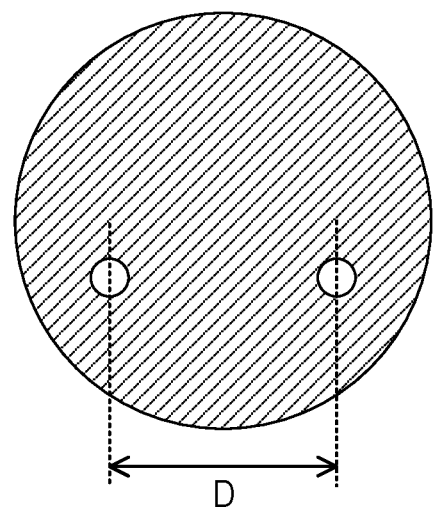
FIGS. 6A and 6B are explanatory diagrams in relation to a method for detecting a position of a subject's eye in a Z direction based on a distance between reflection points of light from a light source.
Figure 6B:
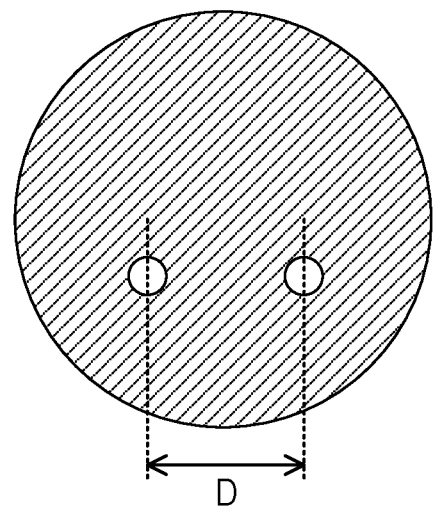

For example, if the distance D is long as shown in FIG. 6A, it means that the distance between the subject's eye E and the head portion 3 is closer as compared to a case where the distance D is short as shown in FIG. 6B. The hatched circular areas shown in FIGS. 6A and 6B each represent the subject's eye E, and the white circular areas therein represent images of the reflected light reflected in the subject's eye E. A relational equation of the distance D and the position of the subject's eye E in the Z direction can be derived from an experiment run in advance or a theoretical calculation.

If the calculated distance D is within a predetermined normal range, the controller 700 determines that it is possible to perform the rough alignment processing in the Z direction. If the calculated distance D is not in the normal range, the controller 700 determines that it is not possible to perform the rough alignment processing in the Z direction.

Determining that it is possible to perform the rough alignment processing in the Z direction (S190: Yes), the controller 700 performs the rough alignment processing in the Z direction based on the position of the subject's eye E in the Z direction which is located from the aforementioned distance D (S200).

Specifically, the controller 700 causes the XYZ-direction driving system 720 to move the head portion 3 in the Z direction so as to align the head portion 3 with a position at a suitable distance away from the position of the subject's eye E in the Z direction (S200). Subsequently, the controller 700 makes the determination in S110. In this case, the position of the head portion 3 relative to that of the subject's eye E is basically within a rage where it is possible to perform the fine alignment processing. Accordingly, the controller 700 makes an affirmative determination in S110 and performs the fine alignment processing (S220).

On the other hand, determining that it is not possible to perform the rough alignment processing in the Z direction (S190: No), the controller 700 prompts the examiner through the display 9 to manually perform the alignment in the Z direction. Upon receipt of operation through the joystick 741, the controller 700 moves the head portion 3 relative to the main body 5 (S210). The examiner can manually align the head portion 3 with the subject's eye E based on the captured image of the anterior segment area of the subject's eye E shown on the display 9.

Upon completion of the above-described manual operation, the controller 700 makes the determination in S110. If the head portion 3 is adjusted by the manual operation to a position where it is possible to perform the fine alignment processing, the controller 700 makes an affirmative determination in S110 and performs the fine alignment processing (S220).

Alternatively, after the process proceeds to S210 and when the rough alignment processing in the Z direction becomes possible as a result of the manual operation, the controller 700 stops receiving the manual operation and performs the rough alignment processing in the Z direction in the same manner as in S200. Subsequently, the controller 700 makes an affirmative determination in S110 and performs the fine alignment processing (S220).

In the fine alignment processing (S220), the controller 700 detects the position of the apex of the cornea of the subject's eye E based on the component of the reflected light of the alignment light included in the image signal from the two-dimensional imaging element 306. The controller 700 further causes the XYZ-direction driving system 720 to move the head portion 3 in the XY directions so as to align the head portion 3 with the detected position of the apex of the cornea of the subject's eye E.

Moreover, the controller 700 controls the second measurement optical system 600 to transmit the second measurement light from the light source 601 and acquires the light-received signals of the reflected light from the light receiving element 604. The controller 700 causes the XYZ-direction driving system 720 to move the head portion 3 in the Z direction so as to suitably align the head portion 3 with the position of the subject's eye E in the Z direction that is located from the component of the reflected light included in the acquired light-received signals. Subsequently, the controller 700 completes the alignment process shown in FIG. 4. Upon completion of the alignment process, the controller 700 may perform ophthalmological examination processes, such as a process to measure the thickness of the cornea and a process to measure the intraocular pressure.

The ophthalmological device 1 according to the present embodiment described above can detect the subject's face placed on the support structure 7 by turning on and off the light sources 301, 302 provided to illuminate the subject's eye E for observation. After the detection, the ophthalmological device 1 can perform the automatic alignment of the head portion 3 with the subject's eye E.

Accordingly, the ophthalmological device 1 can reduce the burden of ophthalmological examinations on the examiner and can promptly and automatically perform preparation for ophthalmological examinations. The automatic performance contributes to shorten the examination time. The present embodiment therefore can provide a highly convenient ophthalmological device.

In the present embodiment, the subject's face is automatically detected, and the head portion 3 is automatically aligned. This can inhibit the head portion 3 from being unnecessarily driven for alignment when the subject's face is not placed on the support structure 7.

Moreover, in the present embodiment, special components are not required for detecting the subject's face. More specifically, without any special hardware, the ophthalmological device 1 can detect the subject's face merely through software processing, such as through the turn-on and turn-off of the light sources 301, 302 and the analysis of the captured image(s). The present embodiment thus enables detection of the subject through the efficient utilization of the structure of the ophthalmological device used for ophthalmological examinations.

The example embodiment of the present disclosure is explained hereinbefore. Nevertheless, the present disclosure is not limited to the aforementioned embodiment and may be embodied in various modes. For example, functions of one component in the aforementioned embodiment may be divided into two or more components. Functions of two or more components may be integrated into one component. A part of the structure of the aforementioned embodiment may be omitted. It should be noted that any and all modes that are encompassed in the technical ideas identified by the languages in the claims are embodiments of the present disclosure.

What is claimed is:

1. An ophthalmological device comprising:
a support structure configured to support a subject's face;
an illumination light source configured to illuminate a subject's eye;

an observation optical system for observing the subject's eye, the observation optical system including an imaging element configured to receive light reflecting off the subject's eye;
a driving system configured to change a position of the observation optical system relative to the support structure; and
a controller, wherein the controller is configured to:
turn on and off the illumination light source;
acquire a first image from the imaging element, the first image being captured by the imaging element when the illumination light source is on;
acquire a second image from the imaging element, the second image being captured by the imaging element when the illumination light source is off;
determine that the subject's face is placed on the support structure when a difference in brightness between the first image and the second image is equal to or larger than a reference value, and determine that the subject's face is not placed on the support structure when the difference in brightness is less than the reference value; and
control the driving system to align the observation optical system with the subject's eye on condition that the subject's face is determined to be placed on the support structure.

2. An ophthalmological device comprising:
a support structure configured to support a subject's face;
an illumination light source configured to illuminate a subject's eye
an observation optical system for observing the subject's eye, the observation optical system including an imaging element configured to receive light reflecting off the subject's eye;
a driving system configured to change a position of the observation optical system relative to the support structure; and
a controller,
wherein the controller is configured to:
turn on and off the illumination light source;
acquire a first image from the imaging element, the first image being captured by the imaging element when the illumination light source is on;
acquire a second image from the imaging element, the second image being captured by the imaging element when the illumination light source is off;
determine whether the subject's face is placed on the support structure based on a difference between the first image and the second image; and
detect a position of a pupil of the subject's eye based on an image captured by the imaging element when the illumination light source is on and control the driving system to align the observation optical system with the subject's eye based on the position of the pupil on condition that the subject's face is determined to be placed on the support structure.

3. The ophthalmological device according to claim 2, wherein the controller determines whether the subject's face is placed on the support structure based on a difference in brightness between the first image and the second image.

4. The ophthalmological device according to claim 2, wherein the controller determines that the subject's face is placed on the support structure when the difference in brightness between the first image and the second image is equal to or larger than a reference value, and determines that the subject's face is not placed on the support structure when the difference in brightness is less than the reference value.

5. An ophthalmological device comprising:
a support structure configured to support a subject's face;
an illumination light source configured to illuminate a subject's eye;
an observation optical system for observing the subject's eye, the observation optical system including an imaging element configured to receive light reflecting off the subject's eye;
a driving system configured to change a position of the observation optical system relative to the support structure;
a position detection system configured to apply light to a cornea of the subject's eye and to receive light reflecting off the cornea so as to detect a position of an apex of the cornea; and
a controller,
wherein the controller is configured to:
turn on and off the illumination light source;
acquire a first image from the imaging element, the first image being captured by the imaging element when the illumination light source is on;
acquire a second image from the imaging element, the second image being captured by the imaging element when the illumination light source is off;
determine whether the subject's face is placed on the support structure based on a difference between the first image and the second image; and
control the driving system to align the observation optical system with the subject's eye on condition that the subject's face is determined to be placed on the support structure,
wherein the controller performs a rough alignment processing and a fine alignment processing so as to align the observation optical system with the subject's eye in a stepwise manner,
wherein the rough alignment processing comprises:
detecting a position of a pupil of the subject's eye based on an image captured by the imaging element when the illumination light source is on, on condition that the subject's face is determined to be placed on the support structure; and
controlling the driving system based on the position of the pupil detected to align the observation optical system with the subject's eye,
wherein the fine alignment processing is performed after the rough alignment processing, and
wherein the fine alignment processing comprises controlling the driving system based on the position of the apex of the cornea acquired from the position detection system to align the observation optical system with the subject's eye.

6. The ophthalmological device according to claim 5, wherein the controller determines that the subject's face is placed on the support structure when the difference in brightness between the first image and the second image is equal to or larger than a reference value, and determines that the subject's face is not placed on the support structure when the difference in brightness is less than the reference value.

* * * * *